United States Patent
Van Bladel et al.

(10) Patent No.: US 6,494,844 B1
(45) Date of Patent: Dec. 17, 2002

(54) DEVICE FOR BIOPSY AND TREATMENT OF BREAST TUMORS

(75) Inventors: Kevin H. Van Bladel, Pleasanton, CA (US); Seth Stabinsky, Pleasanton, CA (US); Lisa Zindel, Pleasanton, CA (US); Glenn Foy, Pleasanton, CA (US); Paul Mikus, Irvine, CA (US)

(73) Assignee: Sanarus Medical, Inc., Pleasanton, CA (US)

( * ) Notice: Subject to any disclaimer, the term of this patent is extended or adjusted under 35 U.S.C. 154(b) by 28 days.

(21) Appl. No.: 09/598,124

(22) Filed: Jun. 21, 2000

(51) Int. Cl.$^7$ ................................................ A61B 10/00
(52) U.S. Cl. ............................................... 600/567
(58) Field of Search .............................. 600/562, 564, 600/567; 604/264, 19, 20, 21, 22–65, 158–177, 236–248, 187; 606/20, 21, 22, 23, 24, 25, 26, 108–115, 167–169, 198; 607/96–107, 108, 115; 128/DIG. 27

(56) References Cited

U.S. PATENT DOCUMENTS

| | | | |
|---|---|---|---|
| 4,644,951 A | 2/1987 | Bays ........................... 128/305 |
| 5,027,827 A | 7/1991 | Cody et al. .................. 128/753 |
| 5,056,523 A | 10/1991 | Hotchkiss, Jr. et al. ..... 128/653 |
| 5,056,532 A | 10/1991 | Hull et al. ................... 128/785 |
| 5,353,804 A | 10/1994 | Kornberg et al. ........... 128/754 |
| 5,429,596 A * | 7/1995 | Arias et al. ................... 604/21 |
| 5,505,210 A * | 4/1996 | Clement ...................... 600/566 |
| 5,649,547 A | 7/1997 | Ritchart et al. ............. 128/754 |
| 5,713,368 A | 2/1998 | Leigh .......................... 128/753 |
| 5,769,086 A | 6/1998 | Ritchart et al. ............. 128/753 |
| 5,868,673 A | 2/1999 | Vesely ......................... 600/407 |
| 5,913,857 A | 6/1999 | Ritchart et al. ............... 600/45 |
| 5,928,164 A | 7/1999 | Burbank et al. ............. 600/567 |
| 5,944,673 A | 8/1999 | Gregoire et al. ............ 600/564 |
| 5,964,716 A | 10/1999 | Gregoire et al. ............ 600/564 |
| 6,007,497 A | 12/1999 | Huitema ...................... 600/567 |
| 6,017,316 A | 1/2000 | Ritchart et al. ............. 600/567 |
| 6,032,675 A | 3/2000 | Rubinsky .................... 128/898 |

FOREIGN PATENT DOCUMENTS

| | | |
|---|---|---|
| WO | WO 97/20504 | 6/1997 |
| WO | WO 98/06346 | 2/1998 |
| WO | WO 00/12009 | 3/2000 |

OTHER PUBLICATIONS

PCT International Search Report dated Nov. 6, 2001.
Biopsys product brochure, *Mammotome® v. ABBI®—A Comparison.*
American Cancer Society breast info webpage, *Vacuum–Assisted Biopsy.*
Americn Cancer Society breast care info webpage, *The ABBI Procedure.*
American Cancer Society breast care info webpage, *Core–Needle Biopsy.*
G.S. Ferzli et al. Advanced Breast Biopsy Instrumentation: A Critique Journal of American College of Surgeons; 1997; 185:145–151.
Edgar D. Staren, MD et al. Ultrasound–guided needle biopsy of the breast. Surgery, Oct. 1999, 629–625.

(List continued on next page.)

*Primary Examiner*—Max F. Hindenburg
*Assistant Examiner*—Pamela Wingwood
(74) *Attorney, Agent, or Firm*—K. David Crockett, Esq.; Crockett & Crockett

(57) ABSTRACT

A device for diagnosis and treatment of tumors and lesions within the body. A cannula adapted to apply suction through the lumen of the catheter to the tumor or lesion is described. The lumen has a self sealing valve through which a cryoprobe is inserted while the suction is being applied. The cryoprobe is then inserted into the lesion, and operated to ablate the lesion.

9 Claims, 5 Drawing Sheets

OTHER PUBLICATIONS

Parker et al. Performing a breast biopsy with a directional, vacuum–assisted biopsy instrument. Radiographics 1997 (Sep. —Oct.), 17 (5) : 1233–52., Abstract Only.

Jackman RJ et al. Needle–Localized breast biopsy: why do we fail? Radiology Sep. 1997, 204(3); 677–84. Abstract Only.

Jackman RJ et al. Percutaneous removal of benign mamographic lesions: comparison of automated large–core and directional vacuum–assited stereotatic biopsy techniques. AJR Am J Roentgenol Nov. 1998, 171 (5), 1325–30, Abstract Only.

Tyco Minimally Invasive Breast Biopsy, 1998.

Bard product brochure, 1995.

Breast care info webpage; Steps in the Mamotome procedure, 1998.

* cited by examiner

DEVICE FOR BIOPSY AND TREATMENT OF BREAST TUMORS

FIELD OF THE INVENTIONS

The devices and method described below relate to the diagnosis and treatment of breast lesions, and more generally, to the diagnosis and treatment of tumors and lesions throughout the body.

BACKGROUND OF THE INVENTIONS

Biopsy is an important procedure used for the diagnosis of patients with cancerous tumors, pre-malignant conditions, and other diseases and disorders. Typically, in the case of cancer, when the physician establishes by means of procedures such as palpation, mammography or x-ray, or ultrasound imaging that suspicious circumstances exist, a biopsy is performed. The biopsy will help determine whether the cells are cancerous, the type of cancer, and what treatment should be used to treat the cancer. Biopsy may be done by an open or percutaneous technique. Open biopsy, which is an invasive surgical procedure using a scalpel and involving direct vision of the target area, removes the entire mass (excisional biopsy) or a part of the mass (incisional biopsy). Percutaneous biopsy, on the other hand, is usually done with a needle-like instrument through a relatively small incision, blindly or with the aid of an imaging device, and may be either a fine needle aspiration (FNA) or a core biopsy. In FNA biopsy, individual cells or clusters of cells are obtained for cytologic examination and may be prepared such as in a Papanicolaou smear. In core biopsy, as the term suggests, a core or fragment of tissue is obtained for histologic examination which may be done via a frozen section or paraffin section. One important area where biopsies are performed is the diagnosis of breast tumors.

Traditionally, the biopsy technique for breast tumors involves placing a biopsy device multiple times into the breast and taking several samples of tissue from a mass or tumor which is suspected of being cancerous. Several samples are required to be sure that some tissue from the suspect mass has been captured, and enough tissue has been sampled to ensure that, if disperse cancer cells exist in the suspect mass some of those cancer cells will be captured in the samples. Each time the device is placed the physician must locate and direct the device with ultrasound imaging into the correct position near the suspect mass. Some breast tumors and lesions are very well defined, hard spherical masses which grow within the soft, compliant breast tissue. It is difficult to force a needle into these lesions because they are resistant to puncture and fairly mobile. Forcing the biopsy needle into the lesion is like trying to spear an apple floating in water.

Vacuum assisted biopsy system proposed by Biopsys involves sucking a breast lesion into a cannula and shearing off the captured edge of the lesion to obtain a biopsy sample. The device uses a vacuum to collect tissue into the side of an open tubular device, and then uses a rotating corer to cut the tissue collected. The rotating corer is slidable within the tubular section and can be pulled back to remove the tissue collected in the rotating corer. An additional stylet inside the rotating core can be used to push the tissue out of the core. The device can be rotated on its axis to remove a sample, 360 degrees around the central placement of the device. Typically, physicians sample six to eight cores. One advantage of this device is that the physician does not have to remove the device for additional biopsy samples. However, the tumor itself must be re-engaged after every coring operation, which entails substantial effort in relocation and confirmation that the target suspect mass has been engaged by the side aperture. Tumors may be too tough to yield to the suction and deform as necessary to enter the side opening of the cannula. Doctors also currently use the device to take a circular sequence of cores by rotating the device about its long axis or by sideways movement of the suction head to take a line of cores.

After biopsy and analysis, the tumor must be treated with a separate device, as Biopsys teaches that their coring device should not be used for resection. Indeed, the device is not designed to perform resection with assurance that complete resection of a suspect mass has been accomplished. Mechanical cutting and disruption of the tissue structure and cancer cell dispersion (that is, tearing of the tissue around the cancer and movement of the cancer cells amongst normal tissue) will result in unintentional delivery of cancer cells into healthy tissue adjacent the lesion.

SUMMARY

The devices and methods described below provide for diagnosis and treatment of tumors within the breast. The devices include structures which permit the surgeon to secure a suspect mass or tumor within the breast for an extended period of time and for several biopsies, coring procedures, or resections. The suspect mass or tumor is secured to a cannula for the entire diagnostic and treatment procedure, or subsets of the procedure such as biopsy or ablation. This allows the placement of the cannula with a single step utilizing methods such as ultrasound to guide the cannula toward the tumor.

The cannula includes a lumen adapted to be connected to a source of vacuum, which can be used to secure a breast lesion to the cannula. A ring seal on the proximal end of the catheter permits biopsy needles, cryoprobes or other ablation devices to be inserted through the cannula and into the lesion while the vacuum on the cannula is maintained. In this manner, the needles and ablation devices may be inserted into the lesion while the lesion in held securely in place by the suction applied to the cannula.

DETAILED DESCRIPTION OF THE INVENTIONS

Figure 1:
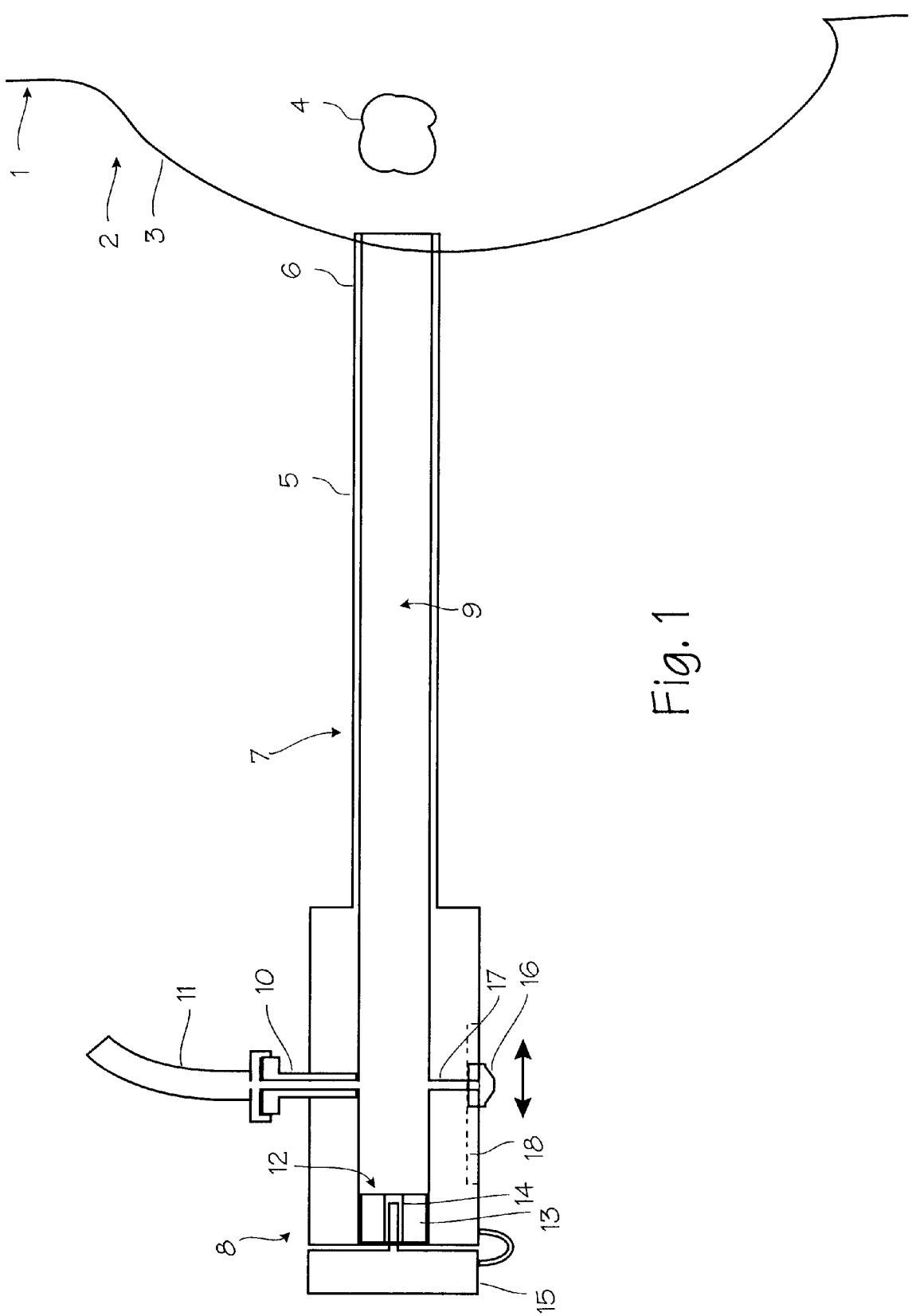
FIG. 1 illustrates the cannula adapted for use in securing a breast tumor during a biopsy or ablation procedure.

FIG. 1 illustrates the biopsy and treatment device adapted for use in securing a breast tumor during the biopsy and 5 treatment procedure. The patient 1 and the patient's breast 2 and skin 3 of the breast are shown schematically. The tumor, lesion or other suspect mass 4 is located within the breast, surrounded by soft tissue and fatty tissue. The tumor in this illustration is a well defined, hard mass ranging in size from 3 to 40 mm in diameter, typical of a benign palpable tumor or fibro-adenoma, although the device and method may be used to treat fibrocystic disease and other conditions. The device comprises a cannula 5 with a straight cut distal edge 6 adapted for insertion through a small incision in the skin overlying the tumor and a proximal end 7 which remains outside the breast. The proximal end of the cannula is fitted with hub 8 which serves as a handle and a manifold for the several connections to the cannula. This hub may be integral with the cannula or provided as a separate piece secured to the proximal end of the cannula. The cannula has a lumen 9 extending through the cannula from the distal edge to the proximal end of the cannula. On the hub, a vacuum connection 10 in the form of Luer fitting provides a fluid connection between the lumen of the cannula and a vacuum hose 11. The vacuum hose may be connected to any source of vacuum or suction. On the proximal end of the hub, a valve 12 seals the cannula proximal end against air pressure but allows passage of the needles and probes used in the procedure. The valve may be a self-sealing silicone plug 13 provided with a slit 14 capable of accommodating the needles and probes by resiliently expanding and conforming around a needle or probe when a needle or probe is forced through the slit, and resiliently closing to an airtight seal when the needles or probes are removed. Thus, the valve allows for insertion of various instruments and elongate medical devices while maintaining the seal necessary to provide sufficient suction to hold the tumor. A stopper or cap 15 is provided for insertion into the slit when the valve is not occupied by a needle or probe to positively seal the valve. A backup valve, such as ball valve which opens to form a clear and straight lumen, may be placed in line before the valve 12 in place of the stopper. The cannula is made of an acceptable biological material such as Teflon™ (polytetrafluoroethylene (PTFE) or expanded polytetrafluoroethylene (ePTFE)), carbon fiber, metal or metal composite for maximum strength with minimal wall thickness. The self-sealing valve is comprised of silicone or other material of similar resilience and conformability. An additional valve 16 may be added on the proximal handle, controlling a port 17 communicating between the vacuum lumen and the exterior of the cannula. The valve illustrated is merely a thumb slide mounted in a recess 18. This valve may be used to break the vacuum established in the vacuum lumen to release a lesion from the distal tip of the device, or to bleed the vacuum from the lumen to lessen the suction on a lesion.

Figure 2:
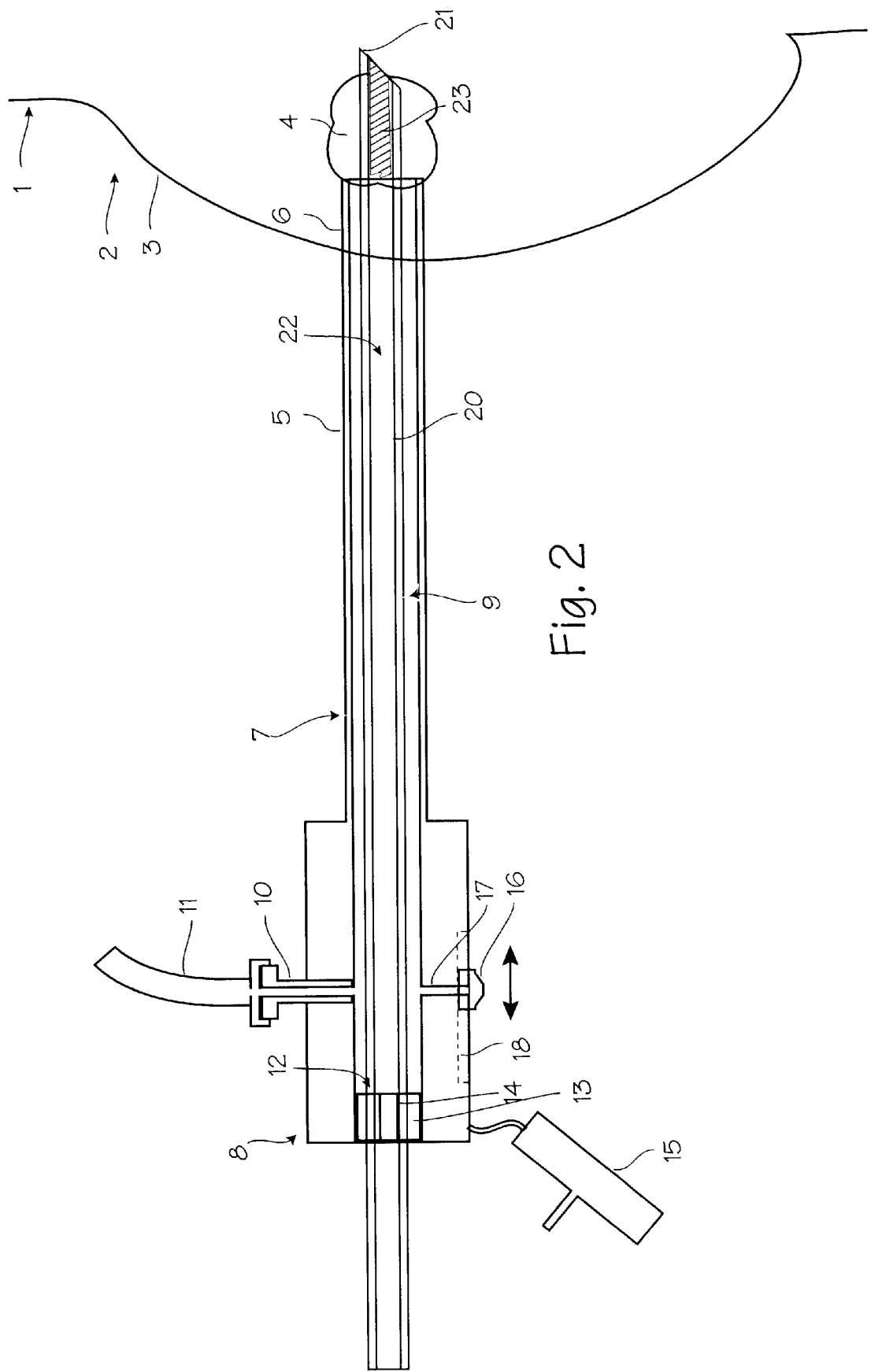
FIG. 2 illustrates the biopsy needle in use with the cannula of FIG. 1.

FIG. 2 illustrates the cannula in use with a biopsy needle 20 in place within the lumen. A biopsy needle 20 fits within the lumen of the cannula and passes through the valve 12. The valve deforms and opens enough to allow the needle to pass through, yet still maintains a sufficiently airtight seal to maintain the vacuum within the cannula lumen. The needle has a sharp distal tip 21 which can pierce the tumor 4. The distal tip is shaped with a coring edge to collect tissue within the lumen 22 of the needle. As depicted in FIG. 2, suction has been applied to the cannula lumen through the vacuum hose 11 and connection 10, thus drawing the tumor to the distal edge of the cannula and securely holding it in place. The biopsy needle has been inserted through the self-sealing valve and through the cannula lumen into and through the tumor. A small core of tumor tissue 23 has been forced into the lumen of the needle. The needle may now be removed and the core of tumor tissue extracted and analyzed for the presence of cancer cells. When the needle is removed, the suction is maintained on the cannula lumen and the tumor remains securely engaged with the cannula distal edge. The biopsy needle (or another) can then be inserted through the cannula and into the tumor without having to relocate and reengage the tumor with the cannula. After all necessary biopsies have been taken, the sample tissue may be analyzed for the presence of cancer cells or other undesirable tissue for which ablation is indicated.

Figure 3:
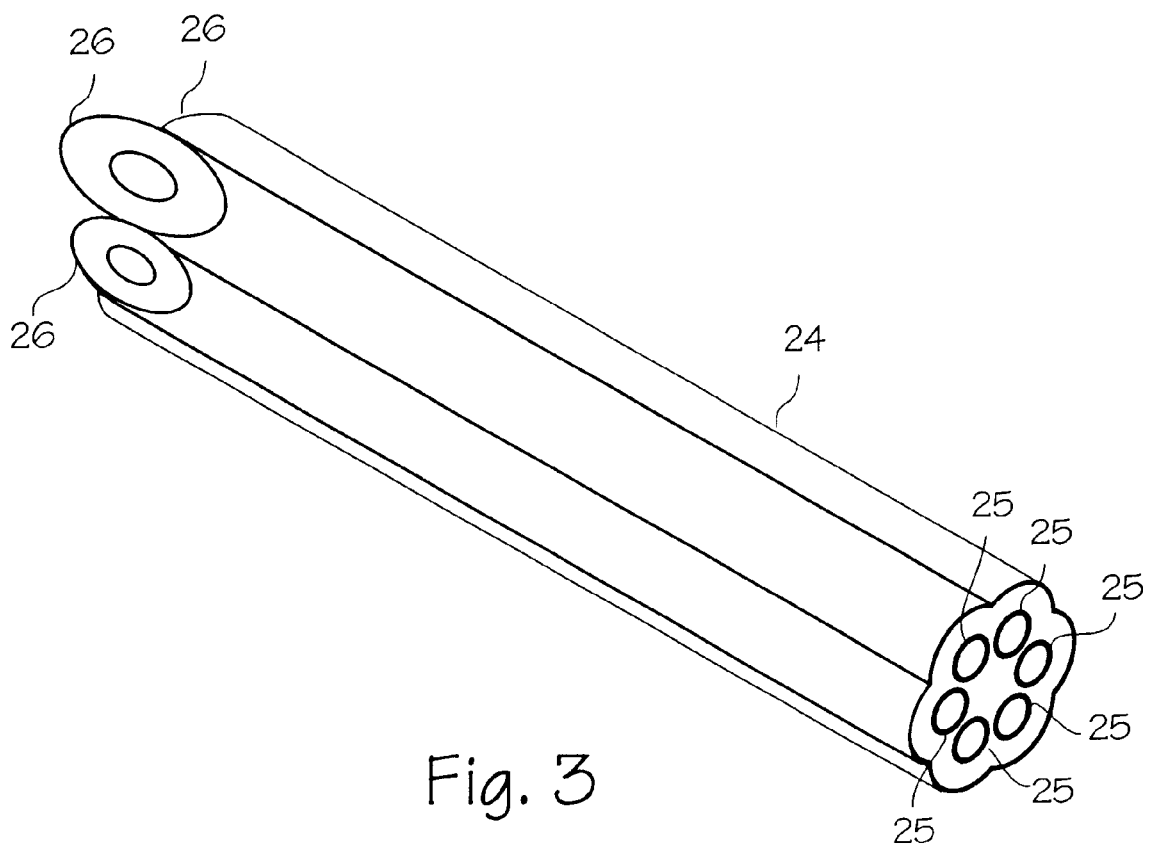
FIG. 3 illustrates a multiple coring needle which may be used with the cannula of FIG. 1.

FIG. 3 illustrates a multiple coring needle 24 for use with the system. This needle includes several coring lumens 25 opening at the distal end of the needle into coring edges 26. The coring lumens are spaced in a circle about the circumference of the needle, and extend from the distal tip 21 of the needle proximally to the proximal end of the needle. It may be used in place of the single biopsy coring needle as illustrated in FIG. 2. By providing suction to one or more of the lumens, the tumor is secured to the coring needle.

Figure 4:
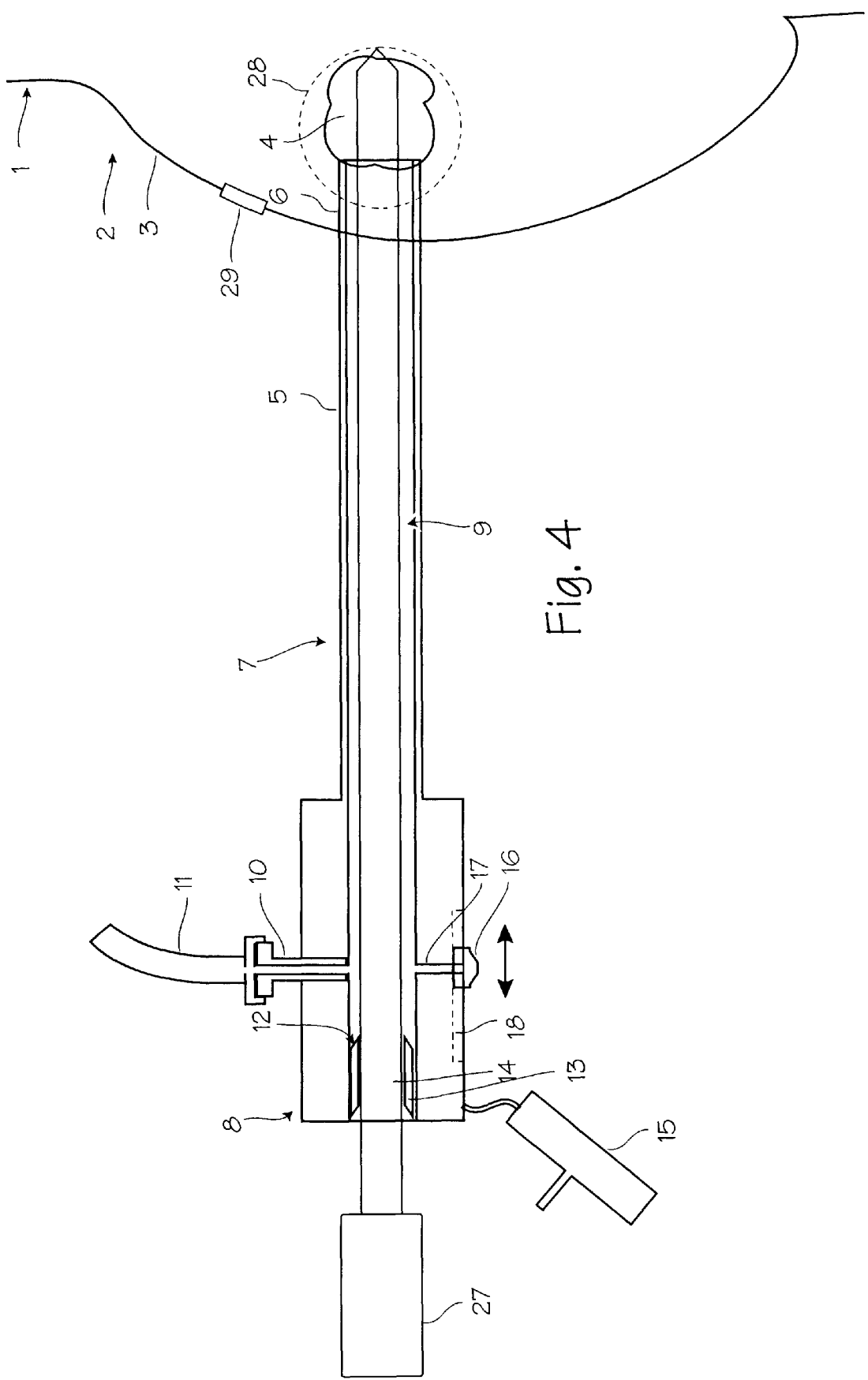
FIG. 4 illustrates the placement of a cryoprobe or other ablative device within the cannula of FIG. 1.

FIG. 4 illustrates the use of an ablative device, such as cryoprobe, with the cannula. The cryoprobe 27 fits within the lumen of the cannula and passes through the valve 12, and the distal tip of the cryoprobe is forced into the tumor until the active freezing portion of the probe resides within the tumor. During placement of the cryoprobe, the vacuum is maintained within the lumen so that the tumor is securely engaged by the cannula. With the tumor secured by the vacuum, the cryoprobe may be easily forced into the tumor. The cryoprobe may be operated to ablate the tumor with cryogenic freezing as required to destroy the tumor. To operate the cryoprobe, liquid or gas cryogenic fluids (such as liquid nitrogen, or gaseous argon in combination with a Joule-Thomson cryostat in the probe tip) are passed through the probe, supplied from a cryosurgical control system (not shown). The operation of the cryoprobe creates an iceball 28 which encompasses the lesion 4, and cools the lesion to lethal cryogenic temperatures. Any ablation device may be used in place of the cryoprobe, including RF ablation probes, microwave ablation probes, laser ablation probes, or focused ultrasound energy probes. Temperature sensors 29 may be mounted on the skin over the lesion in order to monitor skin temperature, so that the surgeon may avoid ablating the skin.

In use, the devices described above are used in place of traditional biopsy, coring and ablation devices. Prior to use, the patient is prepared and the breast is appropriately prepped and draped. The site is prepared using local anesthesia and, optionally, intravenous sedation. The patient is positioned on an operating table in the supine position, with the patient on her back. (If the procedure is accomplished under stereotactic guidance, the patient may be prone on a stereotactic table, exposing the breast below the table.) The breast is imaged, if not previously imaged, to determine the location of lesions. A small incision is made in the breast to allow the cannula to be easily inserted into the skin. The surgeon inserts the cannula into the patient's breast through the incision, pushes it into the breast until the distal edge of the cannula is proximate to the boundary of the tumor. An ultrasound scanner, MRI, stereotactic, mammographic, infrared or other imaging device is used to obtain an image of the breast, including the tumor and any device inserted into the breast, and the surgeon uses the display from the imaging device to assist in guidance of the cannula to the tumor. With the cannula distal edge in position near the tumor, the surgeon applies vacuum to the cannula through the side port on the cannula. The vacuum draws the tumor toward the cannula, and the cannula securely engages the tumor until the suction is broken at the end of the procedure. The surgical biopsy needle can be inserted through the cannula and into the tumor to retrieve a sample of tissue for analysis. Because coring can be accomplished without removing the portion of the tumor engaged by the cannula, or otherwise disrupting the suction between the cannula and the tumor, several biopsy samples may be taken without having to relocate and re-engage the tumor.

Depending on the analysis of the biopsy (whether or not the samples obtained contain cancerous cells or other conditions), treatment of the tumor may be required. If analysis can be accomplished intra-operatively (that is, during a period of time in which it is feasible to keep the patient in the operating room and maintain the tumor engaged with the cannula), and indicates the presence of cancerous cells or other condition for which ablation is indicated, an ablation instrument can be inserted through the cannula and into the tumor. If so, the surgeon inserts an ablation instrument, such as a small caliber cryoprobe, into the tumor. Preferably, the surgeon inserts a cryoprobe through the valve and cannula and into the tumor, while maintaining suction on the cannula. The surgeon initiates cooling of the cryoprobe, and cools the tumor through one or more cycles of cooling to cryogenic temperatures and subsequent warming and thawing. A double freeze-thaw cycle is currently recommended. Each cycle consists of a 6 to 15 minute freeze followed by thawing until the internal cryoprobe temperature reaches 0° C. (approximately 6 to 15 minutes). The device may also be used without regard to biopsy results. Patients prefer to have these lesions treated, even if they prove to be benign. In current practice, should biopsy results indicate the presence of cancer, the patient must return to the operating room shortly after the biopsy, undergo preparation, anesthesia, relocation of the lesion and ablation. Instead, the lesions may be ablated intraoperatively with the biopsy, immediately after biopsy and without interrupting the procedure to await the biopsy results. Should the biopsy prove negative for the presence of cancer, the patient will have received a substantially cosmetic treatment. Should the biopsy prove positive, the patient will have received a necessary therapeutic procedure. In addition to the ablative procedure, the positive biopsy may indicate the need for additional monitoring and treatment.

For lesions deeper than 1 cm from the skin surface, the cryoprobe is advanced until the distal tip is located approximately in the center of the lesion or just beyond the lesion. For smaller lesions (<2 cm diameter) the ice ball may grow beyond the margins of the tumor, while for larger lesions, the ice ball may remain within the confines of the tumor. The cryoprobe tip temperatures and skin mounted thermocouple readings are monitored throughout the ablation procedure. If the temperature of the skin overlying the cryoprobe measures below freezing, freezing operation of the cryoprobes should be paused until it returns to 10° C. (the temperature at the edge of the ice ball edge is 0° C. and exposure to such a temperature for the few minutes will not harm the skin, but caution should always be employed).

The procedure may be augmented with additional steps. Just prior to ablation treatment, prophylactic antibiotics can be administered at the surgeon's discretion. Just prior to cryosurgical ablation, cryogenic enhancement agents may be injected directly into the tumor through a hypodermic needle inserted through the valve and cannula and into the tumor while it is secured by suction to the cannula. During cooling operation of the cryoprobes, warm saline may be washed over the skin overlying the tumor and iceball to prevent freezing of the skin.

Figure 5:
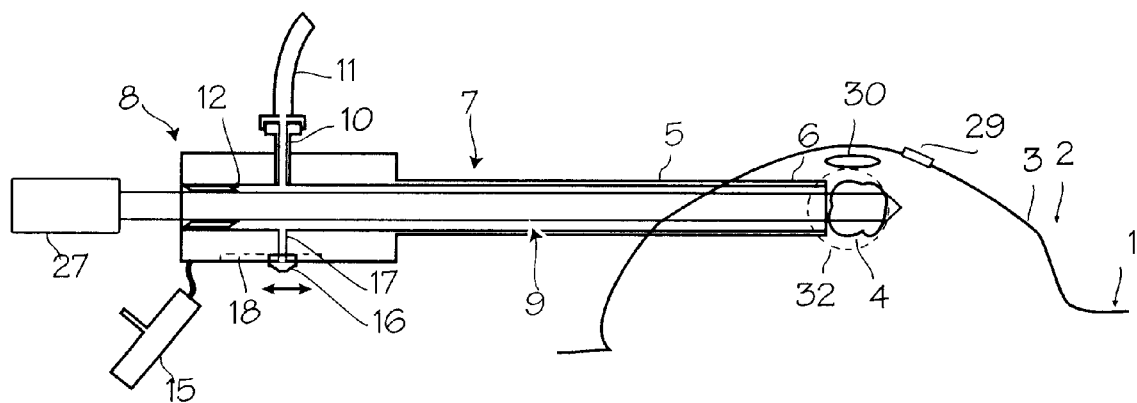
FIG. 5 illustrates a method of breast tumor ablation for tumors located near the skin.
Figure 6:
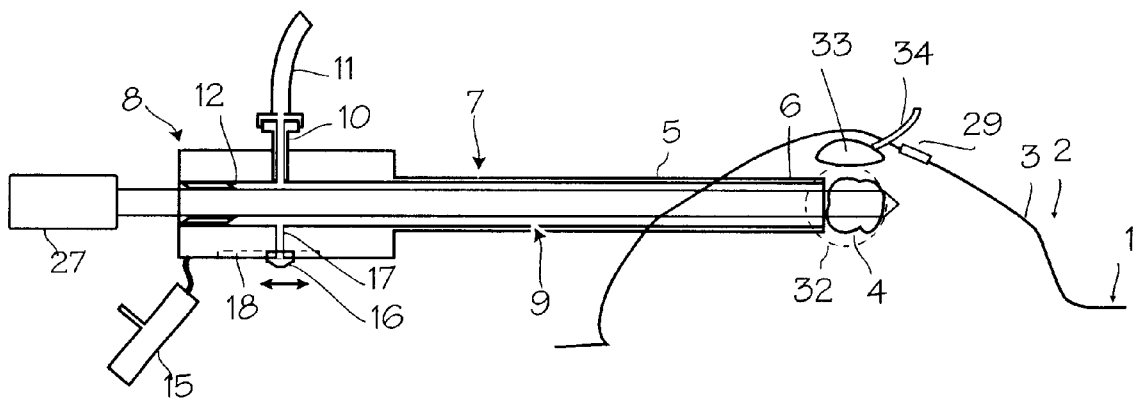
FIG. 6 illustrates a method of breast tumor ablation for tumors located near the skin.

If the lesion being treated is close to the skin such that cryoablation of the lesion entails a danger of cryoablation of the overlying skin, several milliliters of a resorbable material such as sterile saline may be injected or inserted into the subcutaneous tissue between the skin and the lesion. This will create a thermally protective mass or barrier layer between the tumor and the skin. Thermal protection may arise from insulative effect of the thermally protective mass or merely by the distension or separation of the skin away from the tumor and thus away from the iceball. As illustrated in FIG. 5, where the tumor 4 is close to the skin 3, the thermally protective mass 30 is injected between the skin 3 and the subcutaneous fat 31 of the breast. When the cryoprobe 27 is operated to create the iceball, the ice-ball 32 either grows into the thermally protective mass or is inhibited in growth in the direction of the thermally protective mass (as illustrated by the non-spherical shape of the iceball in this illustration). This method basically distends the skin away from the iceball. This may also be accomplished by dissecting the skin away from the tumor with a balloon inserted between the skin and fat in the area overlying the tumor. Balloon dissection can be accomplished as illustrated in FIG. 6. Here, a balloon 33 has been inserted subcutaneously between the tumor 4 and the overlying skin 3. The balloon is inflated with air or other sterile gas, through inflation tube 34, creating a good layer of insulation between the cryoprobe and the overlying skin.

Figure 7:
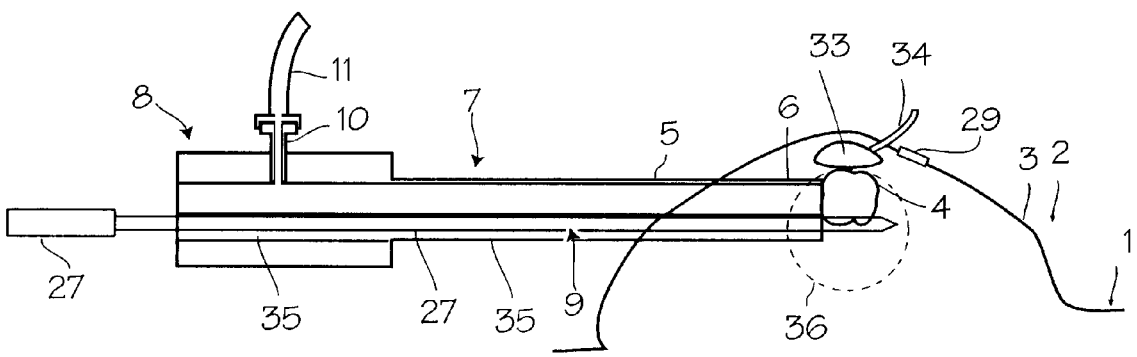
FIG. 7 illustrates and adaptation of the cannula to provide additional protection to the skin.

FIG. 7 illustrates and adaptation of the cannula to provide additional protection to the skin. The cryoprobe 27 is inserted through a side lumen 35 provided on the cannula 5. The breast lesion 4 is drawn by vacuum to the tip of the cannula. The cryoprobe is advances distally out of the side lumen until the freezing region underlies the lesion, and it operated to create the iceball 36. The iceball extends superficially toward the skin and to encompass the lesion, and also extends posteriorly into the breast, where some healthy breast tissue is ablated but the overlying skin is not. This system and procedure also has the advantage that the lesion itself is not punctured, limiting the potential for seeding due to the release of cancerous cells from the disruption of the tissue of the tumor.

The cannula illustrated above is preferably 10 to 20 cm in length and about 3 mm in diameter with an internal diameter of 2.8 mm, and a clearance of about 0.25 mm between the inner bore of the cannula and any device inserted through the cannula during suction. The cryoprobes may be Joule-Thomson probes, liquid cryogen probes, or probes of other designs. Various other ablative devices may be used in place of the cryoprobe, including laser ablation devices, RF ablation devices, chemical ablation catheters and any other ablative technology proposed for use to destroy tumors and lesions. The vacuum applied is preferably in the range of 14 to 21 inches of mercury vacuum.

The devices and methods illustrated above have been illustrated in relation to the treatment of tumors and lesions within the breast. However, they may be used to treat tumors and lesions throughout the body wherever the tumors which are difficult to secure and locate are encountered, and wherever nearby tissue must be protected from freezing. Thus the devices and methods may be used for tumors and lesions of the uterine tube (such as uterine fibroids), kidney, liver, prostate or brain.

Thus, while the preferred embodiments of the devices and methods have been described in reference to the environment in which they were developed, they are merely illustrative of the principles of the inventions. Other embodiments and configurations may be devised without departing from the spirit of the inventions and the scope of the appended claims.

We claim:

1. A system for treating or sampling of a mass within the breast of a human patient, said system comprising:
   a cannula adapted for insertion into the body of the patient, said cannula having a distal end and a proximal end, and a lumen extending through the cannula and defining a proximal opening and a distal opening in the cannula;
   a fitting disposed on the proximal end of the cannula, said fitting adapted for connection to a vacuum source;
   an airtight seal in the proximal opening of the cannula, said airtight seal permitting passage of elongate medical devices through the seal while substantially maintaining the airtight seal;
   a source of vacuum pressure operably connected to the fitting; and
   a biopsy needle capable of insertion through the airtight seal and into the cannula, said biopsy needle being long enough to extend from the proximal end of the cannula to a distance outside the distal opening of the cannula.

2. A system for treating or sampling of a mass within the breast of a human patient, said system comprising:
   a cannula adapted for insertion into the body of the patient, said cannula having a distal end and a proximal end, and a lumen extending through the cannula and defining a proximal opening and a distal opening in the cannula;
   a fitting disposed on the proximal end of the cannula, said fitting adapted for connection to a vacuum source;
   an airtight seal in the proximal opening of the cannula, said airtight seal permitting passage of elongate medical devices through the seal while substantially maintaining the airtight seal;
   a source of vacuum pressure operably connected to the fitting; and
   a cryoprobe capable of insertion through the airtight seal and into the cannula, said cryoprobe being long enough to extend from the proximal end of the cannula to a distance outside the distal opening of the cannula.

3. A method of performing cryosurgery of a lesion in the body of a patient, said method comprising;
   inserting a cannula into the body of the patient so that the distal edge of the cannula is proximate the lesion;
   applying suction to a lumen of the cannula, thereby drawing the lesion toward the cannula;
   inserting an ablative medical device through the lumen of the cannula and into the lesion;
   operating the ablative medical device to ablate the lesion.

4. A method of performing cryosurgery of a lesion in the body of a patient, said method comprising;
   inserting a cannula into the body of the patient so that the distal edge of the cannula is proximate the lesion;
   applying suction to a lumen of the cannula, thereby drawing the lesion toward the cannula;
   inserting a cryoprobe through the lumen of the cannula and into the vicinity of the lesion;
   operating the cryoprobe to ablate the lesion.

5. A method of performing cryosurgery of a lesion in the breast of a patient, the lesion being located under a portion of overlying skin, said method comprising;
   providing a cannula, said cannula having a distal tip and a lumen adapted for applying suction to the distal tip thereof, and inserting the cannula into the body of the patient so that the distal tip of the cannula is proximate the lesion;
   applying suction to a lumen of the cannula, thereby drawing the lesion toward the distal tip of the cannula;
   inserting a cryoprobe into the breast and into the vicinity of the lesion; and
   operating the cryoprobe to ablate the lesion.

6. The method of claim 5 further comprising:
   inserting the cryoprobe into the lesion by inserting it through the lumen of the cannula and then advancing the cryoprobe distally from the lumen of the cannula and into the lesion.

7. The method of claim 5 further comprising:
   inserting the cryoprobe into the lesion.

8. The method of claim 5 further comprising:
   inserting the cryoprobe into the breast in a position posterior to the lesion.

9. The method of claim 5 further comprising:
   placing a thermally protective mass between the lesion and the overlying skin prior to operating the cryoprobe to ablate the lesion.

* * * * *